United States Patent [19]
Cook et al.

[11] Patent Number: 6,020,378
[45] Date of Patent: Feb. 1, 2000

[54] METHOD FOR SELECTIVELY ALTERING BODY FAT LEVEL, FEED EFFICIENTLY, OR WEIGHT GAIN

[75] Inventors: Mark E. Cook, Madison, Wis.; Daria Jerome, Detroit Lakes, Minn.; Michael W. Pariza, Madison, Wis.

[73] Assignee: Wisconsin Alumni Research Foundation, Madison, Wis.

[21] Appl. No.: 09/281,382

[22] Filed: Mar. 30, 1999

[51] Int. Cl.[7] .................................................. A61K 31/20
[52] U.S. Cl. .......................................... 514/560; 514/558
[58] Field of Search ............................................ 514/560

[56] References Cited

U.S. PATENT DOCUMENTS

| | | | |
|---|---|---|---|
| 5,017,614 | 5/1991 | Pariza et al. | 514/558 |
| 5,070,104 | 12/1991 | Pariza et al. | 514/549 |
| 5,428,072 | 6/1995 | Cook et al. | 514/560 |
| 5,430,066 | 7/1995 | Cook et al. | 514/558 |
| 5,554,646 | 9/1996 | Cook et al. | 514/560 |
| 5,760,082 | 6/1998 | Cook et al. | 514/560 |
| 5,851,572 | 12/1998 | Cook et al. | 426/2 |

FOREIGN PATENT DOCUMENTS

| | | |
|---|---|---|
| 6-276939 | 10/1994 | Japan . |
| WO92/10105 | 6/1992 | WIPO . |

OTHER PUBLICATIONS

Belury et al., "Conjugated Linoleic Acid Modulates Hepatic Lipid Composition in Mice", *Lipids*, 32:199–204 (1997).
Cesano et al., "Opposite Effects of Linoleic Acid and Conjugated Linoleic Acid on Human Prostatic Cancer in SCID Mice", *Anticancer Research* 18:1429–1434(1998).
Chen et al., "Chemoenzymatic Synthesis of Conjugated Linoleic Acid", *J. Org. Chem.* 63:9620–9621 (1998).
Chin et al, "Conjugated Linoleic Acid is a Growth Factor for Rats as Shown by Enhanced Weight Gain and Improved Feed Efficiency", *J. Nutri.* 124:2344–2349 (1994).
Chin et al., "Dietary Sources of Conjugated Dienoic Isomers of Linoleic Acid, a Newly Recognized Class of Anticarcinogens", *J. of Food Composition and Analysis* 5:185–197 (1992).
Fogerty et al., "Octadeca–9,11–Dienoic Acid in Foodstuffs and in the Lipids of Human Blood and Breast Milk", *Nutrition Reports International* 38:937–942 (1988).
Gurr, "A Trans Fatty Acid that is Good to Eat? Conjugated Linoleic Acid", *Lipid Technology* 7(6):133–135 (1995).
Ha et al., "Inhibtion of Benzo(α)Pyrene–Induced Mouse Forestomach Neoplasia by Conjugated Dienoic Derivatives of Linoleic Acid", *Cancer Research* 50:1097–1101 (1990).
Ha et al., "Anticarcinogens from Fried Ground Beef: Heat–Altered Derivatives of Linoleic Acid", *Carcinogenesis*, 8(12):1881–1887 (1987).
Ha et al., "Newly Recognized Anticarcinogenic Fatty Acids: Identification and Quantification in Natural and Processed Cheeses", *J. Agric. Food Chem.*, 37(1): 75–81 (1989).
Hayek et al., "Dietary Conjugated Linoleic Acid Influences the Immune Response of Young and Old C57BL/6NCrlBR Mice.", *J. Nutri.*, 129: 32–38 (1999).

Ip et al., "Mammary Cancer Prevention by Conjugated Dienoic Derivative of Linoleic Acid", *Cancer Research* 51:6118–6124 (1991).
Kammerlehner, J. "Linolsaure und Konjugierte Linolsauren–ihr Vorkommen im Milchfett, ihre Biologische Bedeutung", *DMZ Lebensmittelindustrie Und Milchinhaltsstoffe* 116(26):1268–1272 (1995).
Lin et al., "Survey of the Conjugated Linoleic Acid Contents of Dairy Products", *J. Dairy Sci.* 78(11):2358–2365 (1995).
McGuire, "Conjugated Linoleic Acid Concentration of Human Milk and Infant Formulae", *FASEB J.* 10(3):A553 (1996).
Miller et al., "Feeding Conjugated Linoleic Acid to Animals Partially Overcomes Catabolic Responses Due to Endotoxin Injection", *Biochemical and Biophysical Research Communications* 198(3):1107–1112 (1994).
Pariza et al., "Conjugated Linoleic Acid (CLA) Reduces Body Fat", *FASEB Journal* 10(3):A560 (1996).
Pariza, M.W., "CLA, A New Cancer Inhibitor in Dairy Products", *Bulletin of the IDF* 257:29–30(1991).
Pariza, M.W., Food Research Institute 1988 Annual Fall Meeting, Oct. 12, 1998.
Pariza, M.W., "Designer Foods: Effects on Development of Cancer", *J. National Cancer Institute Monographs* 12:105–107 (1992).
Pariza, M.W., "Report of the Council on Scientific Affairs", *Archives of Internal Medicine*, 153:50–56 (1993).
Pariza, M.W., "CLA and HEMF: Newly Recognized Anticarcinogenic Antioxidants", Active Oxygens, Lipid Peroxides, and Antioxidants (Yagi, K. ed., 359–365, Japan Sci. Soc. Press. Tokyo/CRC Press, Boca Raton (1993).
Park et al., "Effect of Conjugated Linoleic Acid on Body Composition in Mice", *Lipids* 32(8):853–858 (1997).
Sarkar, G., "Beneficial ghee?" *Nature* 352:673 (1991).
Shantha et al., "Conjugated Linoelic Acid Concentrations in Processed Cheese Containing Hydrogen Donors, Iron and Dairy–Based Additives", *Food Chemistry* 47:257–261 (1993).
Shanatha et al., "Conjugated Linoleic Acid Concentrations in Dairy Products as Affected by Processing and Storage", *J. Food Science* 60(4):695–720 (1995).
Sieber. R., "Konjugierte Linolsauren in Lebensmitteln: eine Ubersicht", *Ernahrung/Nutrition* 19:265–270 (1996).
Silvis et al., "Nutritional Recommendations for Individuals with Diabetes Mellitus," *South African Med. J.* 81:162–166 (1992).
The Merck Index, Tenth Edition p. 790 (1983).
The Merck Veterinary Manual, Fifth Edition, pp. 1340–1343 and 1374–1379 (1979).

(List continued on next page.)

*Primary Examiner*—Rebecca Cook
*Attorney, Agent, or Firm*—Quarles & Brady LLP

[57] ABSTRACT

A method for treating an animal to reduce body fat while the animal exhibits improved feed efficiency and either continued weight gain or an increase in lean body mass includes the steps of administering to the animal a combination of CLA isomers in a ratio selected to retain a desirable benefit attributable to one isomer while counteracting an undesirable effect of the same isomer.

16 Claims, No Drawings

OTHER PUBLICATIONS

West et al., "Effects of Conjugated Linoleic Acid on Body Fat and Energy Metabolism in the Mouse", *Am. J. Physiol.*, 275 (Regulatory Integrative Comp. Physiol. 44): R667–R672 (1998).

Weyman, C. et al., "Linoleic Acid as an Immunosuppressive Agent," *Lancet*, 2(7923):33 (1975).

Wong et al., "Effects of Dietary Conjugated Linoleic Acid on Lymphocyte Function and Growth of Mammary Tumors in Mice", *Anticancer Research*, 17:987–994 (1997).

METHOD FOR SELECTIVELY ALTERING BODY FAT LEVEL, FEED EFFICIENTLY, OR WEIGHT GAIN

CROSS-REFERENCE TO RELATED APPLICATIONS

Not applicable.

STATEMENT REGARDING FEDERALLY SPONSORED RESEARCH OR DEVELOPMENT

To be determined.

BACKGROUND OF THE INVENTION

The present application generally relates to methods of treating animals, including humans. More particularly, it relates to methods of treating animals to selectively alter body fat, feed efficiency, or weight gain (which can also be measured as growth rate).

CLA is a mixture of isomers that can be formed from 9c,12c-octadecadienoic acid (linoleic acid) which can, theoretically, be autoxidized or alkali-isomerized into 8 conjugated geometric isomers of 9,11- and 10,12-octadecadienoic acid (9c,11c; 9c,11t; 9t,11c; 9t,11t; 10c,12c; 10c,12t; 10t,12c and 10t,12t). The role or roles of individual isomers in particular effects was not previously known because the CLA evaluated in prior studies was a mixture of 9,11-octadecadienoic acids and 10,12-octadecadienoic acids and other CLA isomers. It would be advantageous to clarify these aspects of CLA activity to facilitate preparing novel compositions for administering to animals to maintain a desired biological activity while reducing an undesired activity.

Prior commercial preparations of CLA isomers made from vegetable oil for administration to animals (e.g., CLA-60) typically contain about 20% 10t, 12c-CLA, about 14% 9c, 11t-CLA, and about 66% total CLA isomers. The ratio of 9c, 11t-CLA to 10t, 12c-CLA in such preparations is about 0.7. Other preparations, such as CLA-95 made from 95% linoleic acid, have slightly different isomer ratios. CLA synthesized from linoleic acid or from linoleic-rich oils tend to have ratios of 9c, 11t-CLA to 10t, 12c-CLA of less than 1:1, typically 0.6–0.97 to 1. Such preparations typically contain more 10t, 12c-CLA than 9c, 11t-CLA.

U.S. Pat. No. 5,428,072 discloses a method for increasing the efficiency of converting feed to body weight in an animal which comprises administering to the animal an amount of a conjugated linoleic acid (CLA) mixture effective to increase the efficiency of feed conversion to body weight in the animal.

U.S. Pat. No. 5,554,646 discloses a method for reducing the amount of body fat in an animal by administering to the animal an amount of a CLA mixture effective to reduce the amount of body fat in the animal.

Animals fed standard preparations of CLA consistently gain less weight than non-CLA fed controls. This can be a commercial disadvantage, in that it is often desirable to increase weight gain and rate of gain in animals raised to be food sources. This effect of CLA can be seen in numerous papers including, for example, Wong, M. W., et al., Anti-cancer Research 17:987–994 (1997); Hayek, M. G., et al., J. Nutr. 129:32–38 (1999); West, D. B., et al., Am. J. Physiol. 275 (Regulatory Integrative Comp. Physiol. 44): R667–R672 (1998); Cesano, A., et al., Anticancer Research 18:1429–1434 (1998).

Park, Y. et al, "Effect of Conjugated Linoleic Acid on Body Composition in Mice," Lipids 32:853 (1997) observed reduced body fat and increased lean body mass in mice fed a mixture of CLA isomers, relative to control animals fed corn oil, where the mixture contained approximately equal percentages of the major CLA isomers, namely 9-cis, 11-trans-CLA and 10-trans, 12-cis-CLA. Despite this apparent showing, it is important to note that Park, et al. selected animals having a similar body weight in the reported experiments to avoid introducing changed body weight as a variable in the analysis. Even so, those authors saw slightly reduced body weight in female mice relative to controls.

BRIEF SUMMARY OF THE INVENTION

It is an object of the present invention to disclose compositions that comprise at least two CLA isomers, namely 9c, 11t-CLA and 10t, 12c-CLA, wherein the CLA isomers are present in a ratio effective upon administration to improve feed efficiency and increase lean body mass in an animal without promoting an increase in body fat.

The compositions of the invention comprise at least two CLA isomers, namely 9c, 11t-CLA and 10t, 12c-CLA, in a desirable ratio.

It is another object of the present invention to disclose methods for making the compositions and methods for improving feed efficiency and increasing body mass in an animal without promoting an increase in body fat by administering the compositions of the invention to an animal.

It will be apparent to those skilled in the art that the aforementioned objects and other advantages may be achieved by the practice of the present invention.

BRIEF DESCRIPTION OF THE SEVERAL VIEWS OF THE DRAWINGS

Not applicable.

DETAILED DESCRIPTION OF THE INVENTION

References herein to an "animal" are intended to refer both to immature, growing animals that are gaining weight as part of growth and development and to an adult animal wherein body fat reduction and increased lean body mass are desired. The animals can be, but are not limited to, a rodent, a mammal (such as a bovine, an ovine, a caprine, a primate and a human), and an avian animal (such as a chicken, a duck, a turkey, and a quail).

Animals treated according to the invention have fewer deleterious effects than animals fed CLA mixtures having ratios of the 9c, 11t and 10t, 12c isomers of less than about 1:1. In some cases, treated animals exhibit better feed conversion efficiency than the control animals. Feed conversion efficiency is defined as the amount of feed in grams required to cause an animal to gain 1 gram of weight. A 100 point improvement in feed efficiency corresponds to a decrease of 1 gram in the amount of feed required to cause the animal to gain 1 gram. In view of the substantial market for, e.g., broiler chickens in the U.S. alone (7 billion per year), a point of improvement has significant commercial effect in reduced feed cost. An improvement in feed conversion efficiency within the scope of the invention is an improvement of 5 points or more, preferably at least 10 points, and more preferably at least 50 points over that seen in animals exhibiting deleterious effects on feed efficiency caused by 10t, 12c-CLA.

Animals treated according to the invention also gained weight faster than animals administered the weight-reducing 10t, 12c isomer either alone or with 9c, 11t isomer at any 9c,11t:10t,12c ratio at or below 1:1. A rate of weight gain at least 5% higher than those animals is observed in animals treated according to the invention. In mature animals, the weight gain is attributable to an increase in lean body mass.

Animals treated according to the invention also have a lower wet weight body fat percentage than control animals. A body fat percentage at least 5% lower, more preferably at least 10% lower and most preferably at least 25% lower than control animals is observed in animals treated according to the invention.

While it has been possible to separately observe effects on feed conversion, weight gain and body fat content in an animal by administering a mixture of conjugated linoleic acid isomers to the animal, those skilled in the art have heretofore not known which of the principal CLA isomers (9c, 11t and 10t, 12c) is responsible for which effect or effects. Nor has the interaction between specific isomers, and the effect of administering specific combinations been evaluated. It has also not heretofore been known to use selected amounts or ratios of particular CLA isomers to achieve a desired result.

The inventors have determined and herein disclose that 9c, 11t-CLA isomer administered to an animal has no significant effect on the amount of body fat of the animal, but instead significantly enhances both the efficiency with which feed is converted to weight as well as the rate of weight gain. On the other hand, 10t, 12c-CLA significantly reduces body fat when administered but also significantly suppresses growth and reduces the efficiency with which feed is converted to weight and the rate of weight gain.

This new understanding permits one skilled in the art to produce compositions that comprise specific CLA isomer blends that promote a desirable effect when administered while reducing or eliminating one or more undesirable effects. In particular, an animal will lose body fat while continuing to gain weight and efficiently converting feed to weight if it is administered a composition that comprises 9c, 11t-CLA isomer and 10t, 12c-CLA isomer in a ratio of greater than 1:1, preferably 1.5:1 or more, still more preferably 5:1 or more. Other preferred isomer ratios are 10:1 or more, 20:1 or more, 30:1 or more, 40:1 or more, 50:1 or more, 60:1 or more and 70:1 or more. Because a minimal amount of 10t,12c-CLA isomer must be administered to retain the fat reduction benefit, when the isomer is administered in an animal feed, the feed should contain at least 0.125% of that isomer. Assuming that feed contains 5% total CLA isomers this level can achieved when the ratio of 9c,11t to 10t,12c isomers is about 80:1. At higher ratios, it is necessary to increase the amount of total CLA. While this may be possible, it is generally considered economically undesirable to increase the amount of dietary CLA to more than 5%.

The compositions of the present invention comprise the indicated CLA isomers in a non-natural ratio as specified above, but may also contain other CLA isomers as well as other fatty acids. The isomers can be extracted from natural sources or prepared using enzymatic or biological methods known to those skilled in the art. When making preparations of the invention, the source of the isomers is not critical, one should merely determine that the desired ratio of 9c,11t and 10t,12c isomers is provided in the composition. The commercial CLA can be made from oils having at least 50% linoleic acid and which can contain 95% linoleic acid or more. The cost of CLA isomers increases with increasing purity. Bulk conjugated linoleic acid isomers in a significantly purified form (98%+pure) are commercially available from Matreya, Inc. (Pleasant Gap, Pa.). However, since the source of the isomer is not critical, it is economically advantageous to use the least expensive source of CLA to make preparations according to the invention.

The compositions can comprise one or both of the CLA isomers as a free conjugated linoleic acids or the isomer can be bound chemically through ester linkages such as the triglycerides, methyl and ethyl esters, or as non-toxic salts thereof or other active chemical derivatives of the selected isomers. The free acid is readily converted into a non-toxic salt, such as the sodium, potassium or calcium salts, by reacting chemically equivalent amounts of the free acid with an alkali hydroxide at a pH of about 8 to 9. The isomers are heat stable and can be used as is, or dried and powdered. Some derivatives of individual CLA isomers are also commercially available from Matreya.

The free acid forms of the isomers may be prepared by isomerizing linoleic acid. The non-toxic salts of the free acids may be made by reacting the free acids with a non-toxic base. Natural CLA may also be prepared from linoleic acid by the action of $W^{12}$-cis, $W^{11}$-transisomerase from a harmless microorganism such as the Rumen bacterium *Butyrivibrio fibrisolvens*. Harmless microorganisms in the intestinal tracts of rats and other monogastric animals may also convert linoleic acid to CLA (S. F. Chin, W. Liu, K. Albright and M. W. Pariza, 1992, FASEB J.6:Abstract #2665). No specific method for preparing a mixture of CLA isomers is described herein, since such methods are well known to those skilled in the art. Substantial amounts of individual pure isomers can also be prepared by the method of Chen, C.-A. and C. J. Sih, "Chemoenzymatic Synthesis of Conjugated Linoleic Acid," *J. Org. Chem.* 63:9620 (1998), incorporated herein by reference.

In the method of the present invention for reducing body fat while maintaining feed efficiency and growth rate in an animal, a safe and effective amount of prepared CLA formulations is administered to the animal. Since CLA is a natural food ingredient and it is relatively non-toxic, the amount of CLA which can be administered is not critical as long as it is enough to be effective to achieve the desired outcome noted herein.

The methods of the present invention may take several embodiments. In one embodiment, the CLA is administered to an animal in a pharmaceutical or veterinary composition containing a safe and effective dose of the CLA. In another more preferred embodiment, the animal is fed a food that has been enriched with CLA.

The animal feeds and pharmaceutical preparations for use in the methods of the present invention are those containing the CLA in combination with a conventional animal feed (e.g. poultry feed), human food supplement, or approved pharmaceutical diluent.

The CLA, in addition to being added to an animal's food, can be administered in the form of pharmaceutical or veterinary compositions, such as tablets, capsules, solutions or emulsions to the animal or the humans. The exact amount to be administered, of course, depends upon the form of CLA employed and the route of administration, and the nature of the animal's or human's condition. Generally, the amount of CLA employed as a pharmaceutical will range from about 100 mg to about 20,000 mg of CLA (calculated as the free acids) per day. However, the upper limit of the amount to be employed is not critical because CLA is relatively non-toxic. The amounts of CLA (calculated as the free acids) to be added to food as an additive can range from 0.01% to 2.0% or more by weight of the food. The total amount of CLA isomers added to animal feed is typically about 5% or less.

The practice of the present invention is further illustrated by the following working Examples which are intended to be illustrative, but not limiting on the scope of the invention.

EXAMPLE 1

Highly enriched semi-pure 9c, 11t-CLA (from Matreya) and 10t, 12c-CLA (from Natural) isomers were mixed separately or in combination into a standard mouse diet in the amounts indicated in the following tables (1%=1 g isomer per 100 g of feed). The data collected in this and other Examples were collected in a single large scale protocol. Hence, only six animals were tested in each treatment. The following results were obtained.

When the isomers were administered separately (Tables 1 and 2), it was found that the 10t, 12c-CLA isomer reduced body fat. In contrast, the 9c, 11t-CLA isomer had no effect on body fat. The 9c, 11t-CLA isomer administered in combination with 10t,12c-CLA isomer also did not interfere with the ability of the 10t, 12c-CLA isomer to reduce body fat.

TABLE 1

Effects of 9c, 11t CLA on body fat (± std error of the mean)

| % CLA isomer in feed | | % Body Fat, |
|---|---|---|
| 9c, 11t | 10t, 12c | wet weight |
| 0 | 0 | 14.0 ± 1.7 |
| 0.1 | 0 | 9.9 ± 1.4 |
| 0.2 | 0 | 10.3 ± 2.2 |
| 0.4 | 0 | 13.4 ± 2.0 |

TABLE 2

Effects of 10t, 12c CLA on body fat (± std error of the mean)

| % CLA isomer in feed | | % Body Fat, |
|---|---|---|
| 9c, 11t | 10t, 12c | wet weight |
| 0 | 0 | 14.0 ± 1.7 |
| 0 | 0.1 | 8.8 ± 1.4 |
| 0 | 0.2 | 6.4 ± 1.4 |
| 0 | 0.4 | 3.0 ± .6 |

TABLE 3

Effects of 9c, 11t CLA on ability of 10t, 12c CLA to reduce fat (± std error of the mean)

| % CLA isomer in feed | | % Body Fat, |
|---|---|---|
| 9c, 11t | 10t, 12c | wet weight |
| 0 | 0 | 14.0 ± 1.7 |
| 0 | 0.4 | 3.0 ± .6 |
| 0.2 | 0.4 | 3.1 ± .9 |
| 0.4 | 0.4 | 2.1 ± .6 |

EXAMPLE 2

The 9c, 11t isomer increases gain and improves feed efficiency (Table 4). The 10t,12c isomer reduces feed efficiency and body weight tends to decrease (Table 5).

TABLE 4

Effects of the interaction of 9c, 11t on performance (± std error of the mean)

| % CLA isomer in feed | | Weight Gain | Feed Intake | Feed/Gain (0–3 wks) |
|---|---|---|---|---|
| 9c, 11t | 10t, 12c | (g) (0–3 wks) | (g) (0–3 wks) | (calculated) |
| 0 | 0 | 9.9 ± .9 | 78.3 | 8.00 |
| 0.1 | 0 | 9.8 ± 1.4 | 79.3 | 8.30 |
| 0.2 | 0 | 11.4 ± 1.7 | 85.2 | 6.39 |
| 0.4 | 0 | 11.6 ± 1.8 | 81.4 | 7.51 |

TABLE 5

Effects of the interaction of 10t, 12c on performance (± std error of the mean)

| % CLA isomer in feed | | Weight Gain | Feed Intake | Feed/Gain (0–3 wks) |
|---|---|---|---|---|
| 9c, 11t | 10t, 12c | (g) (0–3 wks) | (g) (0–3 wks) | (calculated) |
| 0 | 0 | 9.9 ± .9 | 78.3 | 8.00 |
| 0 | 0.1 | 9.4 ± .9 | 80.6 | 8.45 |
| 0 | 0.2 | 8.9 ± 2.4 | 74.7 | 8.81 |
| 0 | 0.4 | 9.4 ± 1.3 | 76.1 | 8.92 |

EXAMPLE 3

Surprisingly, the performance limitations of the 10t, 12c-CLA isomer were largely overcome when the isomer was fed in combination with 9c, 11t-CLA isomer in an amount greater than that of the 10t, 12c-CLA isomer. (Table 6) In this example, this is shown at ratios of greater than 2:1.

TABLE 6

Effects of the interaction of c-9, t-11 and t-10, c-12 CLA on body fat, body weight, food consumption and conversion (± std error of the mean)

| % CLA isomer in feed | | % Body Fat, wet weight | Weight Gain (g) (0–3 wks) | Feed Intake (g) (0–3 wks) | Feed/Gain (0–3 wks) (calculated) |
|---|---|---|---|---|---|
| 9c, 11t | 10t, 12c | | | | |
| 0 | 0 | 14.0 ± 1.7 | 9.9 ± .9 | 78.3 | 8.00 |
| 0 | 0.2 | 6.4 ± 1.4 | 8.9 ± 2.4 | 74.7 | 8.81 |
| 0.1 | 0.2 | 8.4 ± 1.8 | 8.2 ± 2.4 | 75.9 | 9.68 |
| 0.2 | 0.2 | 7.4 ± 1.1 | 8.8 ± 1.0 | 72.8 | 8.70 |
| 0.4 | 0.2 | 6.9 ± 1.6 | 9.5 ± .8 | 77.9 | 8.45 |

Accordingly, it is now understood that a CLA oil having a non-natural ratio of 9c, 11t to 10t, 12c isomers of about greater than 1:1, whether obtained from a natural source or prepared by blending purified CLA isomers, is an improved CLA oil for use in a composition or method for reducing body fat without reducing feed efficiency or rate of weight gain. Even though the feed efficiency is not completely restored, it is improved over that seen at isomer ratios less than those of the present invention.

It will be readily apparent to those skilled in the art that a number of modifications or changes may be made without departing from the spirit and scope of the present invention as set forth in the attached claims.

We claim:

1. A method of reducing body fat in an animal without reducing weight gain or feed efficiency, said method comprising administering to said animal a safe and effective amount of a composition comprising 9-cis, 11-trans conjugated linoleic acid and 10-trans, 12-cis conjugated linoleic acid isomers, the composition comprising more 9-cis, 11-trans conjugated linoleic acid isomer than 10-trans, 12-cis conjugated linoleic acid isomer.

2. The method as claimed in claim 1 wherein the isomers are administered orally to the animal in a food.

3. The method as claimed in claim 1 wherein at least one of the isomers is administered as a non-toxic salt of the isomer, as an active ester of the isomer or as a mixture thereof.

4. A method as claimed in claim 1 wherein the animal is selected from the group consisting of a rodent, a mammal, and an avian animal.

5. A method as claimed in claim 4 wherein the mammal is selected from the group consisting of a bovine, an ovine, a caprine, a primate and a human.

6. A method as claimed in claim 4 wherein the avian animal is selected from the group consisting of a chicken, a duck, a turkey, and a quail.

7. A method as claimed in claim 1 wherein the ratio of 9-cis, 11-trans conjugated linoleic acid to 10-trans, 12-cis conjugated linoleic acid isomers is 1.5:1 or more.

8. A method as claimed in claim 1 wherein the ratio of 9-cis, 11-trans conjugated linoleic acid to 10-trans, 12-cis conjugated linoleic acid isomers is 2:1 or more.

9. A method as claimed in claim 1 wherein the ratio of 9-cis, 11-trans conjugated linoleic acid to 10-trans, 12-cis conjugated linoleic acid isomers is 10:1 or more.

10. A method as claimed in claim 1 wherein the ratio of 9-cis, 11-trans conjugated linoleic acid to 10-trans, 12-cis conjugated linoleic acid isomers is 20:1 or more.

11. A composition comprising 9-cis, 11-trans conjugated linoleic acid and 10-trans, 12-cis conjugated linoleic acid isomers, the composition comprising more 9-cis, 11-trans conjugated linoleic acid isomer than 10-trans, 12-cis conjugated linoleic acid isomer.

12. The composition as claimed in claim 11 wherein at least one of the isomers is a non-toxic salt of the isomer, an active ester of the isomer or a mixture thereof.

13. The composition as claimed in claim 11 wherein the 9-cis, 11-trans conjugated linoleic acid and 10-trans, 12-cis conjugated linoleic acid isomers are present in a ratio of 1.5:1 or more.

14. The composition as claimed in claim 11 wherein the 9-cis, 11-trans conjugated linoleic acid and 10-trans, 12-cis conjugated linoleic acid isomers are present in a ratio of 2:1 or more.

15. The composition as claimed in claim 11 wherein the 9-cis, 11-trans conjugated linoleic acid and 10-trans, 12-cis conjugated linoleic acid isomers are present in a ratio of 10:1 or more.

16. The composition as claimed in claim 11 wherein the 9-cis, 11-trans conjugated linoleic acid and 10-trans, 12-cis conjugated linoleic acid isomers are present in a ratio of 20:1 or more.

* * * * *

UNITED STATES PATENT AND TRADEMARK OFFICE
CERTIFICATE OF CORRECTION

PATENT NO. : 6,020,378
DATED : February 1, 2000
INVENTOR(S) : Mark E. Cook; Daria Jerome; Michael W. Pariza It is certified that error appears in the above-identified patent and that said Letters Patent is hereby corrected as shown below:

On the title page, item [54] and column 1, lines 1-4 amend the title to read: --METHOD FOR SELECTIVELY ALTERING BODY FAT LEVEL, FEED EFFICIENCY, OR WEIGHT GAIN--.

Signed and Sealed this

Twenty-fourth Day of October, 2000

Attest:

Q. TODD DICKINSON

*Attesting Officer*         *Director of Patents and Trademarks*